(12) United States Patent
Daoud (10) Patent No.: US 9,970,920 B2
(45) Date of Patent: May 15, 2018

(54) SYSTEMS AND METHODS FOR NON-DESTRUCTIVE TESTING OF ENERGETIC MATERIALS

(71) Applicant: RAYTHEON COMPANY, Waltham, MA (US)

(72) Inventor: Sami Daoud, Tucson, AZ (US)

(73) Assignee: RAYTHEON COMPANY, Waltham, MA (US)

( * ) Notice: Subject to any disclaimer, the term of this patent is extended or adjusted under 35 U.S.C. 154(b) by 245 days.

(21) Appl. No.: 14/730,784

(22) Filed: Jun. 4, 2015

(65) Prior Publication Data

US 2016/0356758 A1    Dec. 8, 2016

(51) Int. Cl.

| | |
|---|---|
| G01J 5/02 | (2006.01) |
| G01N 33/22 | (2006.01) |
| F02K 9/24 | (2006.01) |
| G01N 21/3563 | (2014.01) |
| G01N 21/359 | (2014.01) |
| G02B 23/24 | (2006.01) |
| G01N 21/954 | (2006.01) |
| F02K 9/96 | (2006.01) |

(52) U.S. Cl.
CPC ............... *G01N 33/22* (2013.01); *F02K 9/24* (2013.01); *F02K 9/96* (2013.01); *G01N 21/359* (2013.01); *G01N 21/3563* (2013.01); *G01N 21/954* (2013.01); *G02B 23/2476* (2013.01)

(58) Field of Classification Search
CPC .. G01N 33/22; G01N 21/3563; G01N 21/359; G01N 21/954; F02K 9/24; F02K 9/96; G02B 23/2476

USPC .................................................. 250/339, 301
See application file for complete search history.

(56) References Cited

U.S. PATENT DOCUMENTS

| | | | |
|---|---|---|---|
| 3,329,059 A | 7/1967 | McCormac | |
| 3,690,775 A | 9/1972 | Cousins | |
| 3,937,070 A | 2/1976 | Briar | |
| 5,038,295 A | 8/1991 | Husband et al. | |
| 5,994,691 A * | 11/1999 | Konada ................. | B82Y 20/00 250/234 |

(Continued)

FOREIGN PATENT DOCUMENTS

EP         0385321 A2    9/1990

OTHER PUBLICATIONS

Daoud et al., "Determination of Primary Chemical Constituents of PBX(AF)-108 Warhead Explosive Using microPHAZIR Near Infrared (NIR) Handheld Platform", Annual Conference of the Prognostics and Health Management Society, 2013, pp. 1-11.

(Continued)

*Primary Examiner* — David Porta
*Assistant Examiner* — Abra Fein
(74) *Attorney, Agent, or Firm* — Lando & Anastasi, LLP (57) ABSTRACT

A non-destructive testing system for propellant for a rocket is provided. The system includes an insertion tube having a first end and a second end in addition to a support sleeve configured to mate with a casing of the rocket. The insertion tube includes a channel that extends from the first end to the second end of the insertion tube to receive a probe and also includes a probe tip generally disposed at the second end of the channel. The support sleeve includes an insertion tube opening configured to receive the insertion tube and allow the insertion tube to slide along the support sleeve.

17 Claims, 6 Drawing Sheets

(56) References Cited

U.S. PATENT DOCUMENTS

| | | | |
|---|---|---|---|
| 6,006,163 A | 12/1999 | Lichtenwalner et al. | |
| 6,662,091 B2 | 12/2003 | Wilson et al. | |
| 7,027,953 B2 | 4/2006 | Klein | |
| 7,652,488 B1 | 1/2010 | Lopatin | |
| 8,545,646 B1* | 10/2013 | Sanford | F41A 1/08 |
| | | | 149/108.2 |
| 2004/0193016 A1* | 9/2004 | Root | A61B 1/0052 |
| | | | 600/146 |

OTHER PUBLICATIONS

Daoud et al., "Novel Real-Time Nondestructive Technology for Chemical and Structural Health Management of Solid Rocket Propellants", Prognostics and Health Management (PHM), pp. 1-12.

International Search Report and Written Opinion for corresponding PCT Application No. PCT/US2016/025177 dated Jul. 11, 2016.

Robert B. Moler et al. "Nondestructive Evaluation and Inspection Programs for Pershing II Motors" USACERL Technical Report M-90/16, Jun. 1990, pp. 1-42.

* cited by examiner

SYSTEMS AND METHODS FOR NON-DESTRUCTIVE TESTING OF ENERGETIC MATERIALS

BACKGROUND

Figure 1:
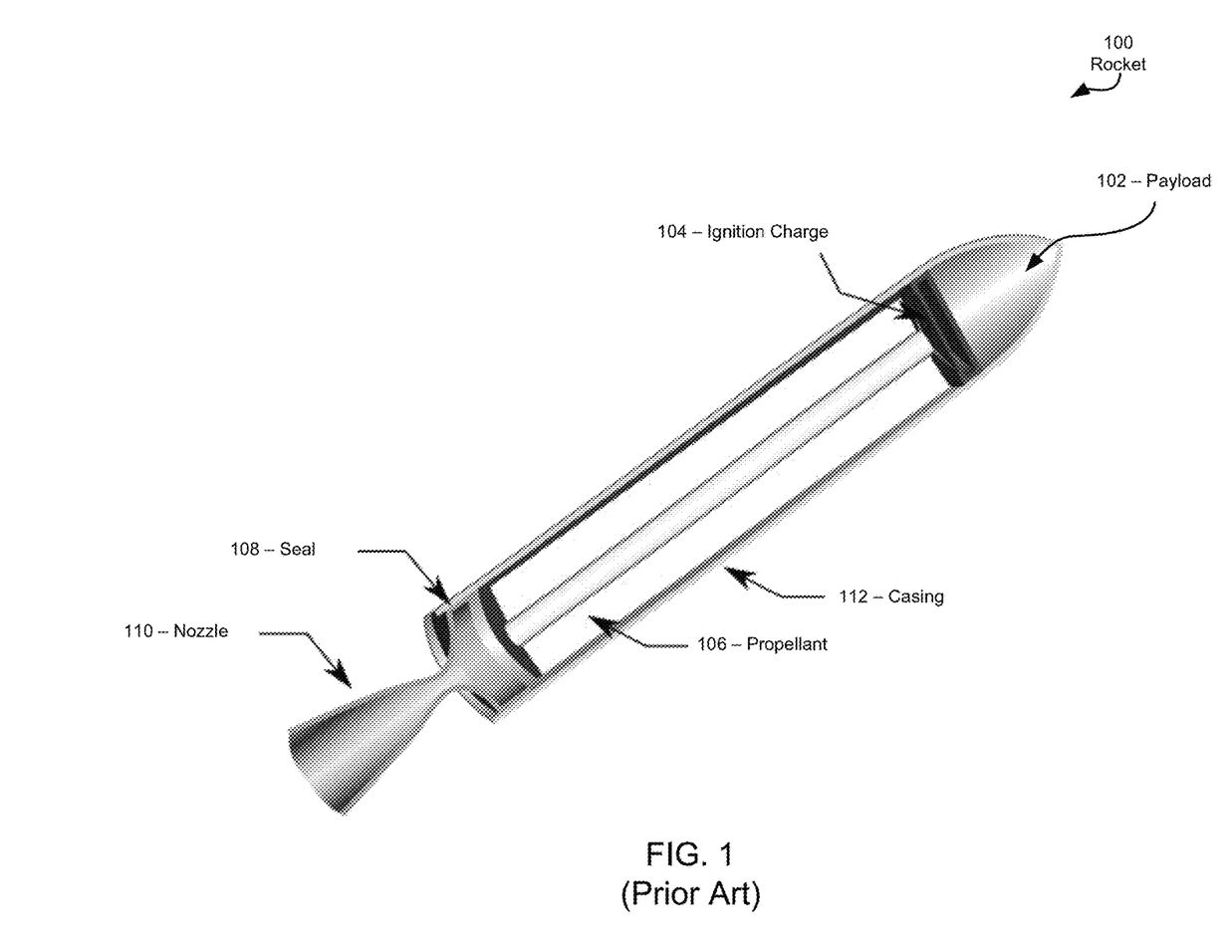
FIG. 1 is an illustration of an example rocket.

Rockets may use an energetic material, such as a propellant, to generate thrust. FIG. 1 illustrates one such rocket 100 that is powered by propellant 106 and constructed to carry a payload 102. The propellant 106 is stored within a casing 112 between the ignition charge 104 and a nozzle 110. The ignition charge 104 ignites the propellant 106 causing exhaust gases to be generated. The exhaust gases are forced through the nozzle 110, thereby generating thrust. A seal 108 between the nozzle 110 and the casing 112 may be included in the rocket 100 to prevent exhaust gases from bypassing the nozzle 110.

The energetic materials in the rocket 100 (e.g., propellant 106) deteriorate when exposed to various stresses encountered in normal service including transportation handling, vibrations, humidity, and temperate changes. As the energetic material deteriorates, the energetic material may undergo dimensional changes and/or cracking potentially causing catastrophic failure of the rocket 100.

The health of energetic materials is generally measured periodically through various destructive tests performed on samples taken from the energetic material. Obtaining these samples requires disassembling the rocket to provide access to the energetic material. The health of the sample may be determined by various bench-top analytical instruments that identify the chemical composition of the sample. Rockets containing energetic materials that are deemed unsafe may be decommissioned.

SUMMARY OF INVENTION

Aspects and examples disclosed herein present real time non-destructive testing systems and methods to measure the health of energetic materials. For instance, some examples use a handheld Near-Infrared (NIR) spectrometer that is configured to analyze the health of energetic materials. In these examples, the handheld NIR spectrometer illuminates a portion of the energetic material with a broad spectrum of light in the NIR region and analyzes light reflected from the energetic material to identify the health of the energetic material. An insertion tube and support sleeve assembly is also provided to enable in situ measurements of propellant within a rocket without complete disassembly of the rocket. The insertion tube slides along the support sleeve into the rocket and directs light from the handheld NIR spectrometer to the propellant and directs the reflected light from the propellant to the handheld NIR spectrometer. Accordingly, the non-destructive testing systems and associated methods disclosed herein reduce the cost and complexity of testing the health of propellant in rockets and other energetic materials.

According to at least one aspect, a non-destructive testing system for propellant for a rocket is provided. The non-destructive testing system includes an insertion tube having a first end and a second end including a first channel extending from the first end to the second end of the insertion tube, the first channel being configured to receive a first probe and a probe tip generally disposed at the second end of the first channel. The non-destructive testing system also includes a support sleeve configured to mate with a casing of the rocket and including an insertion tube opening configured to receive the insertion tube and allow the insertion tube to slide along the support sleeve.

In one example, the support sleeve is configured to mate to an ignition charge mount of the rocket. The support sleeve may include a flange having at least one bolt hole.

In one example, the probe tip is configured to be removable from the insertion tube. In one example, the probe tip is configured to extend towards the propellant and is one of an articulated probe tip and a 90 degree elbow probe tip. In one example, the insertion tube further includes a compression fitting disposed at the first end of the first channel to hold the first probe in place.

In one example, the first probe is an optical fiber probe having a first end connected to the probe tip and a second end. The non-destructive testing system may further include a receptacle configured to receive the second end of the optical fiber probe and optically couple the optical fiber probe to a Near Infrared (NIR) spectrometer. The receptacle may include at least one set screw to hold the second end of the optical fiber probe in place. The optical fiber probe may include a first bundle of optical fibers to carry light from the NIR spectrometer to the probe tip and a second bundle of optical fibers to carry reflected light from the probe tip to the NIR spectrometer. The receptacle may also include a first opening to receive the first bundle of optical fibers and a second opening to receive the second bundle of optical fibers.

In one example, the insertion tube includes a second channel extending from the first end to the second end of the insertion tube, and wherein the second channel is configured to receive a second probe. The second probe may be one of a borescope probe and a hardness probe.

In one example, the insertion tube includes at least one notch to provide an indication of a depth of insertion of the probe tip into the rocket.

In one example, the first probe is an optical fiber probe and the non-destructive testing system further includes a Near Infrared (NIR) spectrometer optically coupled to the optical fiber probe, and wherein the NIR spectrometer is configured to identify a status of the propellant. The NIR spectrometer may include, for example, a handheld NIR spectrometer. The NIR spectrometer may be configured to identify the status of the propellant at least in part by identifying a percentage mass of at least one primary ingredient in the propellant.

According to at least one aspect, a method of non-destructively testing propellant inside a rocket, the method including removing a payload and an ignition charge from the rocket to expose an ignition charge mount of the rocket, mating a support sleeve to the ignition charge mount, inserting an insertion tube into an opening of the support sleeve to extend a probe tip into the rocket, optically coupling a Near Infrared (NIR) spectrometer to an optical fiber probe that extends through the insertion tube, and operating the NIR spectrometer to take at least one NIR measurement of the propellant.

In one example, the act of mating the support sleeve includes bolting the support sleeve to the ignition charge mount on the rocket.

In one example, the act of operating the NIR spectrometer includes operating the NIR spectrometer to provide NIR light to the optical fiber probe, receive light reflected from the propellant, and analyze the light reflected from the propellant to determine a status of the propellant.

Still other aspects, embodiments, and advantages of these exemplary aspects and examples, are discussed in detail below. Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure, or characteristic described may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide illustration and a further understanding of the various aspects and examples, and are incorporated in and constitute a part of this specification, but are not intended as a definition of the limits of the invention. Where technical features in the figures, detailed description or any claim are followed by references signs, the reference signs have been included for the sole purpose of increasing the intelligibility of the figures and description. In the figures, each identical or nearly identical component that is illustrated in various figures is represented by a like numeral. For purposes of clarity, not every component may be labeled in every figure. In the figures:

DETAILED DESCRIPTION

The following examples describe systems and methods of non-destructive testing for energetic materials. For instance, some examples disclosed herein manifest an appreciation that the health of energetic materials needs to be continuously measured to ensure safe operation of the device carrying the energetic material. Accordingly, some examples disclosed herein include a handheld NIR spectrometer configured to measure the health of energetic materials and an insertion tube to provide easy access to propellant inside a rocket. Thereby, the health of energetic materials can be measured without completely disassembling the device holding the energetic material or obtaining a sample of the energetic material. Further, the health of the energetic material can be immediately assessed without waiting for results from bench-top analytical instruments.

It is to be appreciated that examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other example.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Figure 2A:
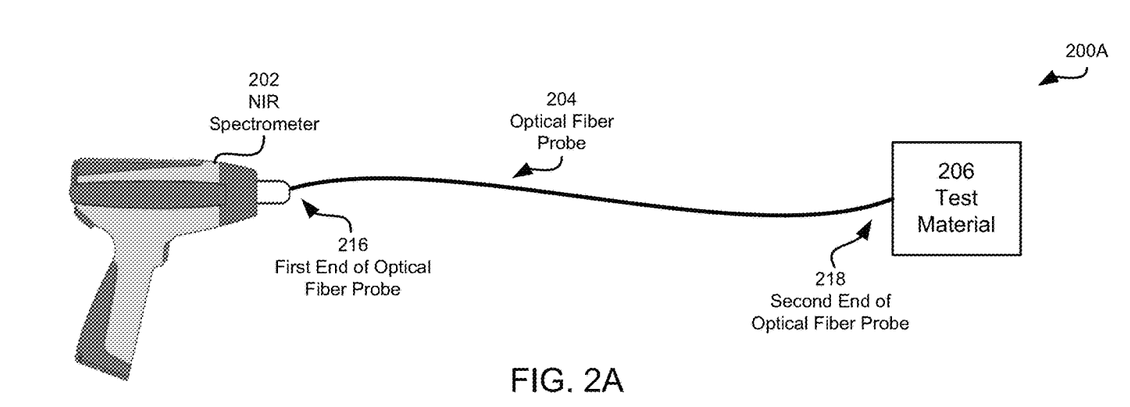
FIG. 2A is an illustration of an example non-destructive testing system.

FIG. 2A illustrates an example non-destructive testing system 200A constructed to test the health of test material 206. The test material 206 may be an energetic material including, for example, a propellant or an explosive. The non-destructive testing system 200A includes a NIR spectrometer 202 and optical fiber probe 204. The optical fiber probe 204 includes a first end 216 optically coupled to the NIR spectrometer 202 and a second end 218 that is proximate or touches the test material 206. The optical fiber probe 204 carries light from the NIR spectrometer 202 to the test material 206 and also carries reflected light from the test material 206 to the NIR spectrometer 202. It is appreciated that the optical fiber probe 204 may be removed from the non-destructive testing system 200A and the NIR spectrometer 202 may be placed proximate or touching the test material 206.

The NIR spectrometer 202 provides NIR light that illuminates the test material 206 and analyzes the light reflected from the test material 206 to identify the composition. The NIR light that has a frequency bandwidth that includes a frequency of the vibration of a molecule in the test material 206 is generally absorbed. The components of the test material 206 may be identified by analyzing the reflected light to identify particular frequencies that are absorbed by the test material 206. The NIR light provided by the NIR spectrometer 202 includes light with a wavelength between 800 nm and 2500 nm. Employing NIR light may be advantageous because it is less likely to heat the energetic material relative to other wavelengths of light. Heating the energetic material is undesirable because it increases the risk of the energetic material igniting and/or combusting. The NIR light may be generated by, for example, a 5 Watt tungsten bulb with an operating temperature range between 5 degrees centigrade and 40 degrees centigrade to avoid ignition of the energetic material.

Suitable NIR spectrometers include various portable NIR spectrometers such as the handheld microPHAZIR™ NIR spectrometer manufactured by Thermo Fisher Scientific. These commercially available NIR spectrometers, however, are generally only suitable for identifying the presence of a single compound in a scanned product. Energetic materials, however, have multiple primary ingredients that need to be simultaneously measured. The percentage mass of each primary ingredient in an energetic material has a tolerance range defined by a specification associated with the energetic material. Energetic materials with one or more primary ingredients outside of the tolerance range defined by the specification generally must be decommissioned. The portable NIR spectrometers may be used as platform where various models may be loaded to enable energetic material health monitoring capabilities. These models may be generated by measuring the NIR spectra of various compositions of the energetic material that fall within the specification as described further below with reference to FIG. 5.

Figure 2B:
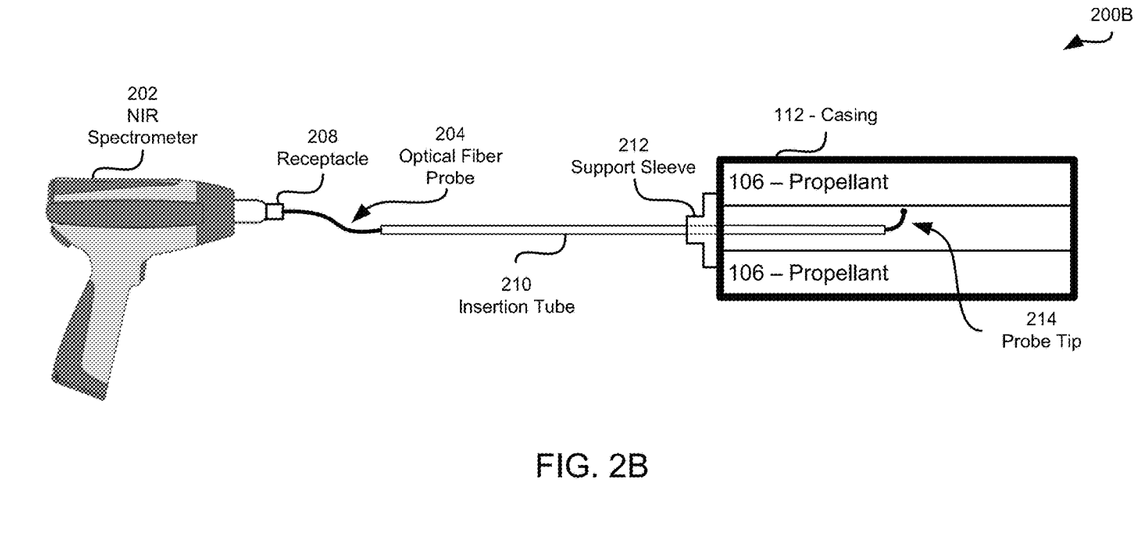
FIG. 2B is an illustration of another example non-destructive testing system.

FIG. 2B illustrates another example non-destructive testing system 200B that is constructed to test the health of propellant 106 inside a casing 112 of a rocket. The non-destructive testing system 200B includes a NIR spectrometer 202, an optical fiber probe 204, a receptacle 208, an insertion tube 210, a support sleeve 212, and a probe tip 214. The receptacle 208 is an interface between the NIR spectrometer 202 and the optical fiber probe 204 that holds the strands of the optical fiber probe 204 in the appropriate location in front of the NIR light emitter and reflected light detector of the NIR spectrometer 202. The optical fiber probe 204 extends into the insertion tube 210 and terminates at the probe tip 214. The probe tip 214 is configured to extend toward the propellant 106 and emit NIR light from the optical fiber probe 204.

In some examples, the insertion tube 210 is supported by the support sleeve 212 that can be attached to the rocket casing 112. The support sleeve 212 allows the insertion tube 210 to slide into and out of the rocket casing 112. The support sleeve 212 may be installed by removing both the payload and the ignition charge from the rocket and mating or mounting the support sleeve 212 to the mount for the ignition charge. Constructing the support sleeve 212 to connect to a pre-existing mount on the rocket allows the non-destructive testing system 200B to be compatible with existing rocket designs. The support sleeve 212 in combination with the insertion tube 210 is configured to provide access to the propellant 106 without complete disassembly of the rocket.

Figure 3A:
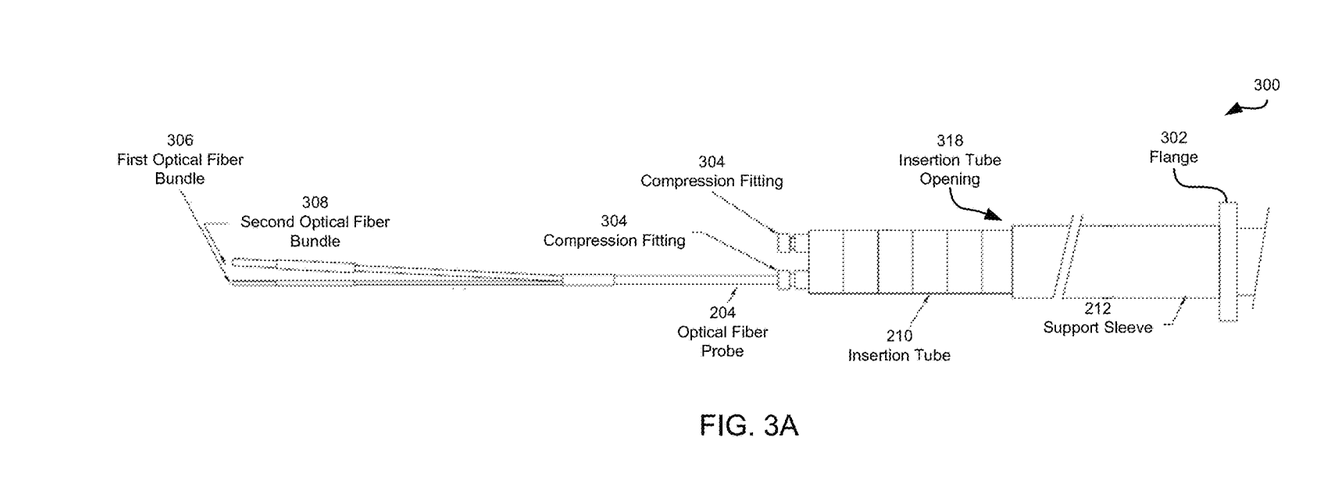
FIGS. 3A and 3B are an illustration of an example insertion tube and support sleeve assembly.
Figure 3B:
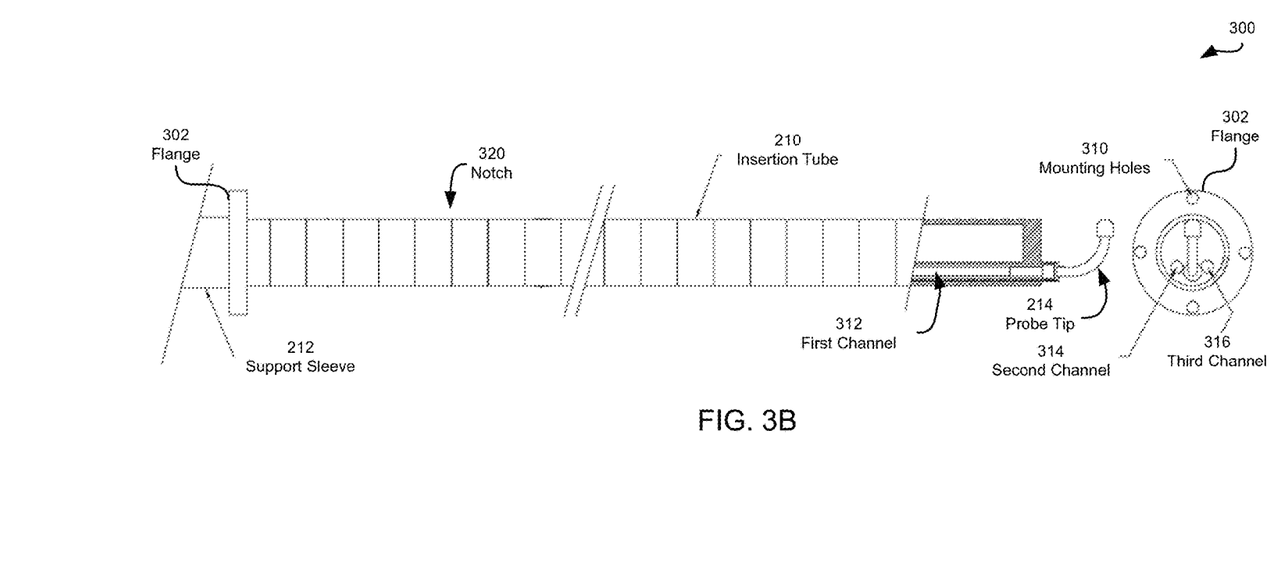

FIGS. 3A and 3B illustrate an example insertion tube and support sleeve assembly 300. The support sleeve and insertion tube assembly 300 includes a support sleeve 212 that is constructed to receive an insertion tube 210. As illustrated in FIGS. 3A and 3B, the support sleeve 212 includes a flange 302 with, for example, four mounting holes 310. The flange 302 in combination with the mounting holes 310 enables the support sleeve 212 to be mated to a casing of a rocket. For example, the pattern of the mounting holes 310 may be constructed to be identical to an existing hole pattern on the rocket to mount the ignition charge. In this example, the flange 302 of the support sleeve 212 may be easily mated to the rocket using the ignition charge mount. It is appreciated that other mounting systems may be employed depending upon the particular construction of the rocket.

The support sleeve 212 includes an insertion tube opening 318 to receive the insertion tube 210. The insertion tube opening 318 may be a circular opening constructed to allow the insertion tube 210 to slide into and out of the support sleeve 212. An external surface of the insertion tube 210 may include a series of evenly spaced notches 320. The notches 320 may be used by an operator to identify how far the insertion tube 210 has been inserted into the rocket. The notches 320 may also be labeled with the distance between a particular notch 320 and the probe tip 214.

The insertion tube 210 includes one or more channels that extend along the length of the insertion tube to receive various probes. As illustrated in FIG. 3B, the insertion tube includes a first channel 312, a second channel 314, and a third channel 316 to receive various probes. The first channel 312 may be constructed to receive an optical fiber probe 204 that is held in place by a compression fitting 304. The optical fiber probe 204 extends through the first channel 312 and terminates at a probe tip 214 that directs NIR light emitted from the optical fiber probe 204 towards the propellant within the rocket casing. The probe tip 214 may be, for example, a 90 degree elbow probe tip or an articulated probe tip. Using an articulated probe tip may be advantageous because the stand-off distance between the probe tip 214 and the propellant 106 is reduced thereby minimizing light scattering and improving performance. The second channel 314 and the third channel 316 may be employed for other probes including, for example, a hardness probe and a borescope probe. It is appreciated that compression fittings 304 may also be employed to hold probes inserted into the second channel 314 and/or the third channel 316. In addition, the number of channels in the insertion tube may be altered based on the number of probes used to measure or observe the propellant.

Figure 4:
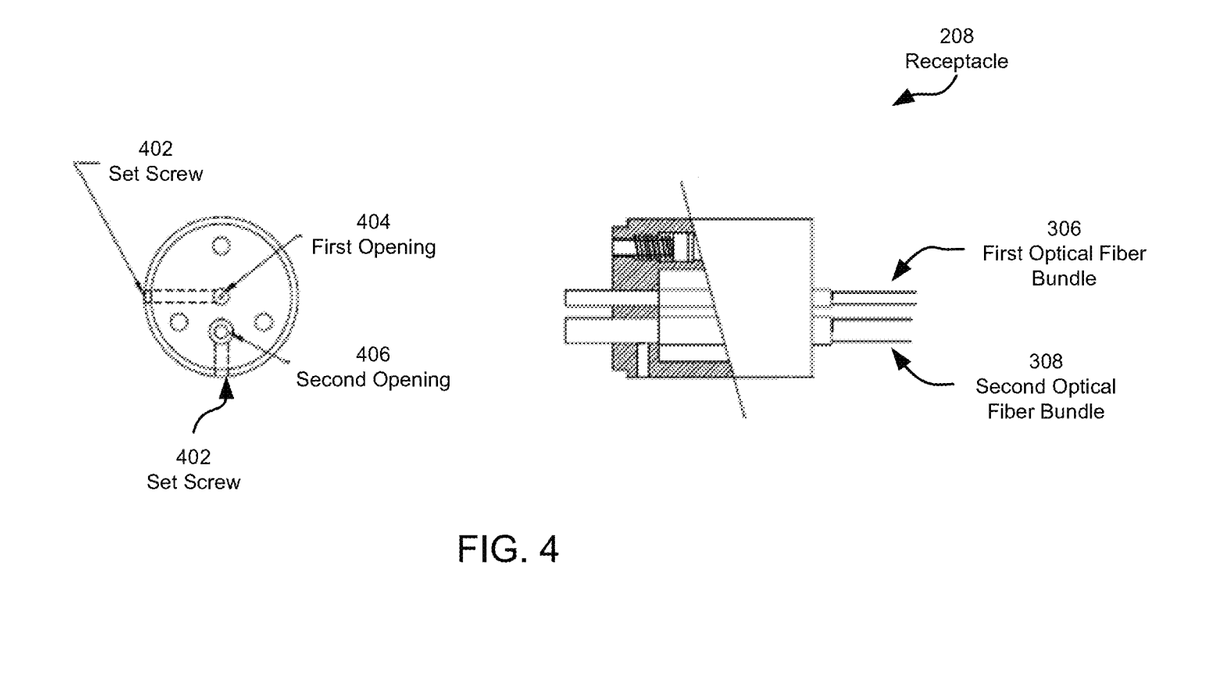
FIG. 4 is an illustration of an example receptacle.

The optical fiber probe 204 includes a first optical fiber bundle 306 to carry light from an output of a NIR spectrometer to the propellant and a second optical fiber bundle 308 to carry reflected light the propellant back to the NIR spectrometer. Referring to FIG. 4, a receptacle 208 may be constructed to align the first optical fiber bundle 306 and the second optical fiber bundle 308 of the optical fiber probe 204 with the NIR light emitter and reflected light detector of the NIR spectrometer 202. The receptacle 208 includes a first opening 404 and a second opening 406 to receive the first optical fiber bundle 306 and the second optical fiber bundle 308, respectively. The optical fiber bundles 306 and 308 may be held in place by set screws 402.

Figure 5:
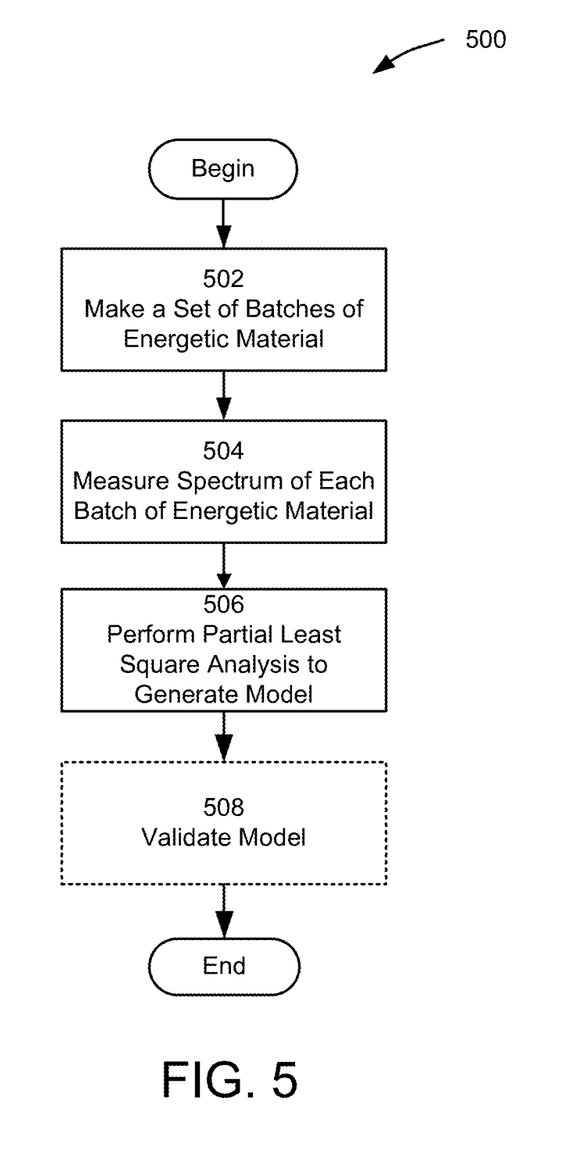
FIG. 5 is a flow chart of an example process for building a model for a NIR spectrometer.

As discussed above, the NIR spectrometer illuminates a sample with broadband NIR light and analyzes the light reflected from the sample to identify the composition. The NIR spectrometer may require various reference models in order to identify the particular composition of an energetic material with multiple primary ingredients. FIG. 5 illustrates an example process 500 to build a model for a NIR spectrometer. The model building process 500 includes an act 502 of making a set of batches of energetic material, an act 504 of measuring the spectrum of each batch of energetic material, and an act 506 of performing a partial least square analysis to generate the model. The model building process 500 may also include an optional act 508 of validating the model.

In act 502, a set of batches of the energetic material are created. Each batch of energetic material may be representative of a unique combination of the primary ingredients that falls within the acceptable range for the energetic material (e.g., defined by a specification). For example, the energetic material being measured may include a propellant for a rocket with a set of primary ingredients including an oxidizer, a plasticizer, a stabilizer, and a binder. The specification for the propellant may specify an upper and lower bound for each of the four ingredients as illustrated below in table 1.

TABLE 1

| Ingredient | Lower Bound (Percentage Mass) | Upper Bound (Percentage Mass) |
| --- | --- | --- |
| Oxidizer | 79.4% | 84.6% |
| Plasticizer | 5.1% | 5.5% |
| Stabilizer | 0.48% | 0.52% |
| Binder | 9.41% | 15.02% |

Given the specification for the energetic material, a set of batches may be generated that covers the range of each primary ingredient defined by the specification. Each of the identified batches may be made into a standardized shape including, for example, a rectangular prism and/or a cube. An example set of batches for the primary ingredients identified in table 1 is illustrated below in table 2.

TABLE 2

| Sample # | Oxidizer | Plasticizer | Stabilizer | Binder |
|---|---|---|---|---|
| 1 | 79.4 | 5.1 | 0.48 | 15.02 |
| 2 | 79.4 | 5.3 | 0.52 | 14.78 |
| 3 | 79.4 | 5.5 | 0.51 | 14.59 |
| 4 | 79.4 | 5.4 | 0.5 | 14.7 |
| 5 | 80.7 | 5.4 | 0.49 | 13.41 |
| 6 | 80.7 | 5.1 | 0.51 | 13.69 |
| 7 | 80.7 | 5.2 | 0.52 | 13.58 |
| 8 | 80.7 | 5.3 | 0.48 | 13.52 |
| 9 | 82 | 5.4 | 0.51 | 12.09 |
| 10 | 82 | 5.1 | 0.49 | 12.41 |
| 11 | 82 | 5.5 | 0.5 | 12 |
| 12 | 82 | 5.2 | 0.48 | 12.32 |
| 13 | 83.3 | 5.5 | 0.48 | 10.72 |
| 14 | 83.3 | 5.3 | 0.5 | 10.9 |
| 15 | 83.3 | 5.2 | 0.49 | 11.01 |
| 16 | 83.3 | 5.4 | 0.52 | 10.78 |
| 17 | 84.6 | 5.3 | 0.51 | 9.59 |
| 18 | 84.6 | 5.5 | 0.49 | 9.41 |
| 19 | 84.6 | 5.2 | 0.5 | 9.7 |
| 20 | 84.6 | 5.1 | 0.52 | 9.78 |

In act 504, each batch is measured by a NIR spectrometer (e.g., NIR spectrometer 202). Multiple measurements may be performed on each batch to improve the accuracy of the resulting model. The measurements by the NIR spectrometer may be used as the basis to perform the linear regression analysis in act 506. It is appreciated that the measured spectra may be filtered to reduce noise and/or artifacts before applying least square analysis in act 506. The measured spectra may be filtered by applying, for example, baseline correction, normalization, and/or smoothing techniques.

In act 506, the measurements taken by the NIR spectrometer are analyzed by applying least square analysis to generate a model. Least square analysis identifies a relationship between a dependent variable with one or more independent variables by generating curve that best fits a given data set. The curve minimizes the sum of the square error between the curve and the data points. The curve may be represented by equation (1) below:

$$y = \alpha + \beta_1 * X_1 + \beta_2 * X_2 + \ldots \beta_n * X_n \quad (1)$$

In equation (1), the term y is the dependent variable that is represented as a combination of independent variables $X_1$ through $X_n$. The terms $\beta_1$ through $\beta_n$ are coefficients associated with the independent variables $X_1$ through $X_n$. The term $\alpha$ is a constant that is the y-intercept of the model. The independent variables may include the percentage composition of each primary ingredient and the dependent variable may include the resulting spectra shapes and/or spectra intensity. The coefficients $\beta_1$ through $\beta_n$ are representative of the sensitivity of the spectra shapes and/or spectra intensity to changes in the concentration of the respective primary ingredients $X_1$ through $X_n$. Each of the coefficients $\beta_1$ through $\beta_n$ may be identified individually based on a subset of the batches where the concentration of one primary ingredient is altered while the concentration of the other primary ingredients is held relatively constant. These identified coefficients may be combined into a model consistent with equation (1). The completed model may be loaded onto the NIR spectrometer to identify the composition of the energetic material associated with the model.

In optional act 508, the model may be validated by comparing the performance of the NIR spectrometer with the loaded model to the performance of traditional destructive testing methods. For example, the NIR spectrometer with the model may be operated to measure the composition of additional batches of the energetic material. The measurements generated by the NIR spectrometer may be compared with measurements from a bench-top High-Performance Liquid Chromatography (HPLC) instrument on the same batches of energetic material. If the measurements from the NIR spectrometer are similar to the measurements from the HPLC, the model is valid. Otherwise, the model may be generated again by, for example, repeating process 500.

Figure 6:
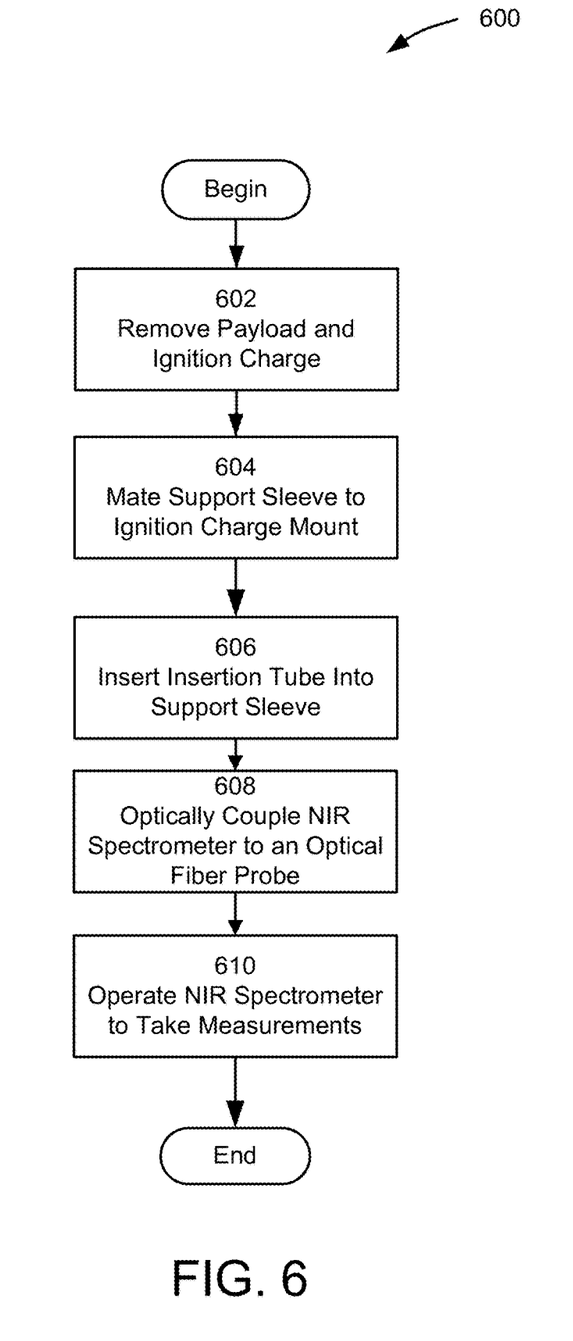
FIG. 6 is a flow chart of an example process for in situ testing propellant in a rocket.

As discussed above with reference to FIGS. 3A and 3B, an insertion tube and support sleeve assembly provides easy access to propellant within a rocket without complete disassembly of the rocket. FIG. 6 illustrates an example process for in situ testing propellant in a rocket 600 using the insertion tube and support sleeve assembly. The propellant testing process 600 includes an act 602 of removing the payload and ignition charge, an act 604 of mating the support sleeve to the ignition charge mount, an act 606 of inserting the insertion tube into the support sleeve, an act 608 of optically coupling a NIR Spectrometer to an optical fiber prove, and an act 610 of operating the NIR spectrometer to take measurements.

In act 602, the payload and the ignition charge are removed from the rocket. Removing the payload and ignition charge provides access to the propellant through an opening in the casing and exposes an ignition charge mount on the casing. The support sleeve is mated to the ignition charge mount on the casing in act 604. Mounting the support sleeve may include aligning bolt holes on a flange of the support sleeve with bolt holes on the casing and bolting the support sleeve to the casing.

In act 606, an insertion tube is inserted into the support sleeve to extend a probe tip of the insertion tube into the rocket. The insertion tube may be slid along the support sleeve a specified length into the rocket based on the particular area of the propellant being tested. An operator may measure the distance the insertion tube has been inserted into the rocket by the notches on the external surface of the insertion tube.

In act 608, an NIR spectrometer is optically coupled to an optical fiber probe that extends through a channel of the insertion tube to the probe tip. The optical fiber probe may be optically coupled to the NIR spectrometer by connecting a receptacle to the NIR spectrometer and/or placing the receptacle proximate the NIR spectrometer. The NIR spectrometer may be operated to take measurements of the propellant in act 610. Operating the NIR spectrometer may include operating the NIR spectrometer to provide NIR light to the optical fiber probe, receive NIR light reflected from the propellant, and analyze the NIR light reflected from the propellant to determine a status of the propellant.

Each of the processes disclosed herein depicts one particular sequence of acts in a particular example. Some acts are optional and, as such, may be omitted in accord with one or more examples. Additionally, the order of acts can be altered, or other acts can be added, without departing from the scope of the systems and methods discussed herein.

Having described above several aspects of at least one example, it is to be appreciated that various alterations, modifications, and improvements will readily occur to those skilled in the art. For example, the systems and associated methods disclosed herein may be adapted to non-destructively test other energetic materials including warhead explosives and/or liquid rocket propellants. Such alterations, modifications, and improvements are intended to be part of this disclosure and are intended to be within the scope of the invention. Accordingly, the foregoing description and drawings are by way of example only.

What is claimed is:

1. A non-destructive testing system for propellant for a rocket comprising:
    an insertion tube having a first end and a second end including:
        a first channel extending from the first end to the second end of the insertion tube, the first channel being configured to receive an optical fiber probe that includes a first bundle of optical fibers and a second bundle of optical fibers;
        a probe tip generally disposed at the second end of the first channel, wherein the first bundle of optical fibers extends into the insertion tube and terminates at a first end of the optical fiber probe at the probe tip to carry light to the probe tip, and wherein the second bundle of optical fibers extends into the insertion tube and terminates at the first end of the optical fiber probe at the probe tip to receive reflected light from the propellant; and
    a support sleeve configured to mate to an ignition charge mount of the rocket, the support sleeve including an insertion tube opening configured to receive the insertion tube and allow the insertion tube to slide along the support sleeve.

2. The non-destructive testing system of claim 1, wherein the support sleeve includes a flange having at least one bolt hole.

3. The non-destructive testing system of claim 1, wherein the probe tip is configured to be removable from the insertion tube.

4. The non-destructive testing system of claim 1, wherein the probe tip is configured to extend towards the propellant and is one of an articulated probe tip and a 90 degree elbow probe tip.

5. The non-destructive testing system of claim 1, wherein the insertion tube further includes a compression fitting disposed at the first end of the first channel to hold the optical fiber probe in place.

6. The non-destructive testing system of claim 1, further comprising a receptacle configured to receive a second end of the optical fiber probe and optically couple the optical fiber probe to a Near Infrared (NIR) spectrometer.

7. The non-destructive testing system of claim 6, wherein the receptacle includes at least one set screw to hold the second end of the optical fiber probe in place.

8. The non-destructive testing system of claim 6, wherein the first bundle of optical fibers is configured to carry the light from the NIR spectrometer to the probe tip and the second bundle of optical fibers is configured to carry the reflected light from the probe tip to the NIR spectrometer.

9. The non-destructive testing system of claim 8, wherein the receptacle includes a first opening to receive the first bundle of optical fibers and a second opening to receive the second bundle of optical fibers.

10. The non-destructive testing system of claim 1, wherein the insertion tube includes a second channel extending from the first end to the second end of the insertion tube, and wherein the second channel is configured to receive a second probe.

11. The non-destructive testing system of claim 10, wherein the second probe is one of a borescope probe and a hardness probe.

12. The non-destructive testing system of claim 1, wherein the insertion tube includes at least one notch to provide an indication of a depth of insertion of the probe tip into the rocket.

13. The non-destructive testing system of claim 1, wherein the non-destructive testing system further comprises a Near Infrared (NIR) spectrometer optically coupled to the optical fiber probe, and wherein the NIR spectrometer is configured to identify a status of the propellant.

14. The non-destructive testing system of claim 13, wherein the NIR spectrometer includes a handheld NIR spectrometer.

15. The non-destructive testing system of claim 13, wherein the NIR spectrometer is configured to identify the status of the propellant at least in part by identifying a percentage mass of at least one primary ingredient in the propellant.

16. A method of non-destructively testing propellant inside a rocket, the method comprising:
    removing a payload and an ignition charge from the rocket to expose an ignition charge mount of the rocket;
    mating a support sleeve to the ignition charge mount, including bolting the support sleeve to the ignition charge mount on the rocket;
    inserting an insertion tube into an opening of the support sleeve to extend a probe tip into the rocket;
    optically coupling a Near Infrared (NIR) spectrometer to an optical fiber probe that extends through the insertion tube to the probe tip, wherein the optical fiber probe includes a first bundle of optical fibers that extend from the NIR spectrometer into the insertion tube and terminate at the probe tip, and a second bundle of optical fibers that extend from the NIR spectrometer into the insertion tube and terminate at the probe tip; and
    operating the NIR spectrometer to take at least one NIR measurement of the propellant including carrying light from the NIR spectrometer along the first optical fiber bundle to the optical fiber probe, and carrying light reflected from the propellant to the NIR spectrometer along the second optical fiber bundle.

17. The method of claim 16, wherein operating the NIR spectrometer includes analyzing the light reflected from the propellant to determine a status of the propellant.

* * * * *